United States Patent [19]

Leeper et al.

[11] Patent Number: 4,568,343

[45] Date of Patent: Feb. 4, 1986

[54] SKIN PERMEATION ENHANCER COMPOSITIONS

[75] Inventors: Harold M. Leeper, Mountain View; Diane Nedberge, Los Altos; Lina T. Taskovich, Palo Alto, all of

[73] Assignee: Alza Corporation, Palo Alto, Calif.

[21] Appl. No.: 659,121

[22] Filed: Oct. 9, 1984

[51] Int. Cl.$^4$ ............................................. A61K 9/00
[52] U.S. Cl. ................................... 604/896; 424/28; 604/897; 514/946; 514/552
[58] Field of Search ................. 604/890, 896, 897; 424/27, 28, 307

[56] References Cited

U.S. PATENT DOCUMENTS

| | | | |
|---|---|---|---|
| 3,472,931 | 10/1969 | Stoughton et al. | 424/180 |
| 3,527,864 | 9/1970 | MacMillan et al. | 424/177 |
| 3,598,122 | 8/1971 | Zaffaroni | 128/268 |
| 3,598,123 | 8/1971 | Zaffaroni | 128/268 |
| 3,896,238 | 7/1975 | Smith | 424/358 |
| 3,903,256 | 9/1975 | MacMillan et al. | 424/59 |
| 3,952,099 | 4/1976 | Smith | 424/227 |
| 4,046,886 | 9/1977 | Smith | 424/227 |
| 4,130,643 | 12/1978 | Smith | 424/238 |
| 4,130,667 | 12/1978 | Smith | 424/361 |
| 4,144,317 | 3/1979 | Higuchi et al. | 424/21 |
| 4,201,211 | 5/1980 | Chandrasekaran et al. | 604/897 |
| 4,286,592 | 9/1981 | Chandrasekaran | 128/260 |
| 4,299,826 | 11/1981 | Luedolers | 424/181 |
| 4,314,557 | 2/1982 | Chandrasekaran | 128/260 |
| 4,335,115 | 6/1982 | Thompson et al. | 424/181 |
| 4,343,798 | 8/1982 | Fawzi | 424/240 |
| 4,379,454 | 4/1983 | Campbell et al. | 604/897 |
| 4,405,616 | 9/1983 | Rajadhyaksha | 424/244 |
| 4,435,180 | 3/1984 | Leeper | 604/896 |
| 4,460,372 | 7/1984 | Campbell et al. | 604/897 |

FOREIGN PATENT DOCUMENTS 1001949 8/1965 United Kingdom .......... 424/248.55

OTHER PUBLICATIONS

Norman F. Estrin, "CTFA Cosmetic Ingredient Dictionary", 1973, 1st Edition, pp. 126 and 127.
Idson, "Percutaneous Absorption", Journal of Pharmaceutical Sciences, Jun. 1975, pp. 901–924.

Primary Examiner—Andrew H. Metz
Assistant Examiner—Terryence Chapman
Attorney, Agent, or Firm—Steven F. Stone; Paul L. Sabatine; Edward L. Mandell

[57] ABSTRACT

A method for enhancing the transdermal flux of a transdermally deliverable drug through intact skin is described in which the drug is delivered simultaneously with polyethylene glycol monolaurate. Preferred embodiments of transdermal therapeutic systems for delivering drug and polyethylene glycol monolaurate employ matrix containing drug at a concentration above saturation.

16 Claims, 2 Drawing Figures

SKIN PERMEATION ENHANCER COMPOSITIONS

FIELD OF THE INVENTION

This invention relates to the transdermal delivery of drugs or other biologically active agents and more particularly to novel methods and compositions for enhancing the permeability of skin or other body surfaces to biologically active agents.

RELATED PATENT APPLICATION

This invention is related to the invention disclosed in copending, coassigned patent application of Cheng, et al. of like date herewith for Transdermal Therapeutic Systems for the Administration of Naloxone, Naltrexone and Nalbuphine.

BACKGROUND OF THE INVENTION

The transdermal route of parenteral delivery of drugs provides many advantages and transdermal systems for delivering a wide variety of drugs or other beneficial agents are described in U.S. Pat. Nos. 3,598,122, 3,598,123, 4,379,454, 4,286,592 and 4,314,557, for example, all of which are incorporated herein by reference. In many cases, drugs which would appear to be ideal candidates for transdermal delivery are found to have such low permeability through intact skin that they cannot be delivered at therapeutically effective rates from reasonably sized systems. In an effort to increase skin permeability it has been proposed to pretreat the skin with various chemicals or to concurrently deliver the drug in the presence of a permeation enhancers. Various materials have been suggested for this purpose as described in U.S. Pat. Nos. 4,299,826, 4,343,798, 4,046,886, 4,130,643, 4,405,616, 4,335,115, 4,130,667, 3,903,256, 4,379,454, 3,527,864, 3,952,099, 3,896,238, 3,472,931 which are incorporated herein by reference, British Pat. No. 1,001,949 and Idson, Percutaneous Absorption, J. Phar. Sci., Vol. 64, No. b 6, June 1975, pp. 901-924 (particularly 919-921). To be considered useful a permeation enhancer should possess certain characteristics in addition to its ability enhance the permeability of at least one and preferably a large number of drugs. These characteristics include being non-toxic, non-irritating on prolonged exposure and under occlusion, and non-sensitizing on repeated exposure. Preferably it shuld also be odorless and capable of delivering drugs without producing burning or tingling sensations.

According to our invention, we have discovered that polyethylene glycol monolaurate (PEGML), an emollient composition presently listed in the Cosmetic Ingredient Directory, is highly effective in enhancing the permeation of a large number of drugs and other therapeutic or beneficial agents through body surfaces and membranes, generally, and skin, particularly, and when formulated in pharmaceutical compositions with other materials appears to satisfy the criteria noted above.

It is accordingly an object of our invention to increase the permeability of body surfaces of animals and humans, including the mucosa and other membranes and more particularly of human skin, to the transport of drugs and other beneficial agents by the concurrent application of the drug or beneficial agent and PEGML to the body surface.

It is another object of our invention to provide compositions of matter for application to the skin which comprise PEGML and a transdermally deliverable drug or beneficial agent.

It is another object of our invention to provide transdermal therapeutic systems for the concurrent delivery of PEGML and a drug or beneficial agent.

These and other objects and advantages will be readily apparent from the following description with reference to the accompanying drawings wherein:

DESCRIPTION OF THE INVENTION

Figure 1:
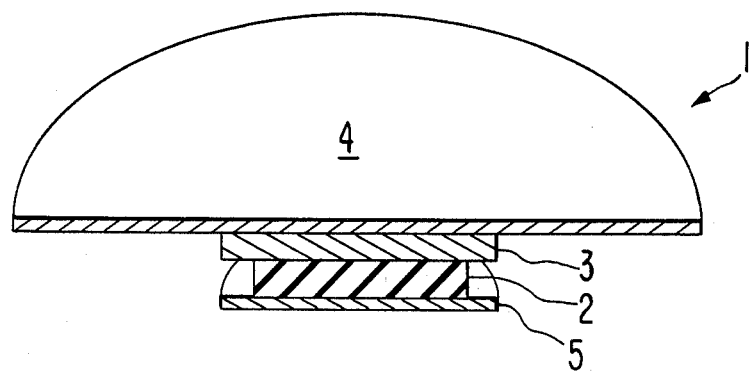
FIG. 1 is a cross-sectional, perspective view through one embodiment of transdermal therapeutic system according to this invention.

According to our invention we have discovered that PEGML can be used to enhance the permeability to drugs and other beneficial agents of body surfaces generally and, more particularly, to enhance the transdermal permeability of a multiplicity of drugs useful in the treatment of a wide variety of conditions and indications. As used herein the term "drug" relates to a biologically active agent, compound or composition of matter which is administered for the purpose of providing some beneficial or therapeutic effect. As used herein the term "transdermal" delivery relates to the delivery of a drug by passage through intact skin into the vascularized layers below the stratum corneum for absorption by the blood stream. Thus transdermal delivery is distinguished from topical application to the surface of intact skin for topical treatment or to application to open wounds or to skin lacking the stratum corneum such as burned or abraded skin.

According to our invention PEGML and the drug to be delivered are placed in drug and PEGML transmitting relationship to the appropriate body surface, preferably in a carrier therefor, and maintained in place for the desired period of time. The drug and PEGML are typically dispersed within a physiologically compatible matrix or carrier as more fully described below which may be applied directly to the body as an ointment, gel, cream, suppository or sublingual or buccal tablet for example but are more preferably administered from a transdermal therapeutic system as more fully described below.

We have also found that PEGML, in addition to its known low toxicity and colorless and odorless nature, does not sensitize skin on repeated exposure. Further, it can be applied to the skin in compositions that do not produce irritation even on occlusion and repeated application to the same site and is capable of enhancing drug flux without producing objectionable skin sensations.

PEGML has utility in connection with the delivery of drugs within the broad class normally delivered through body surfaces and membranes, including skin. In general, this includes therapeutic agents in all of the major therapeutic areas including, but not limited to, anti-infectives, such as antibiotics and antiviral agents, analgesics and analgesic combinations, anorexics, anthemidines, antiarthritics, antiasthmatic agents, anticonvulsants, antidepressants, antidiabetic agents, antidiarrheals, antihistamines, antiinflammatory agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, beta-blockers, antiarrythmics, antihypertensives, diuretics, vasodilators including general, coronary, peripheral and cerebral, central nervous system stimulants, cough and cold preparations, decongestants, diagnostics, hormones, hypnotics, immunosuppressives, muscle relaxants, parasympatholytics, parasympathomimetics, psychostimulants, sedatives and tranquilizers.

We have demonstrated the utility of PEGML as a permeation enhancer for a large number of dissimilar drugs within these classes and believe it to be applicable to an even larger number of such drugs including, by way of example and not for purposes of limitation; scopolamine, isosorbide dinitrate, nitroglycerin, estradiol, clonidine, cortisone, hydrocortisone, theophylline, phenylephrine, terbutaline, ephedrine, narcotine, quinidine, estradiol diacetate, progesterone, pilocarpine, furosemide, tetracycline, insulin, chlorpheniramine, sulfathiazides, propranolol, testosterone, norgestrel, lidocaine, morphinone, morphine, dihydrocodeine, dihydromorphine, oxycodone, hydrocodone, codeine, norcodeine, hydromorphine, normorphine, norlevorphanol, dihydrothebaine, ouabain, bromocryptine, haloperidol, guanabenz, salbutamol, oxprenolol, tetracaine, dibucaine, altenolol, pindolol, and timolol, for example as well as to other drugs not specifically noted herein.

The effect of PEGML as a permeation enhancer for other drugs not specifically set forth herein, may be readily determined by a worker skilled in the art from in vitro permeation measurements performed on cadaver skins or other membranes in conventional diffusion cell tests as well as by in vivo measurements of blood or urine levels for example.

PEGML is available in various grades differing primarily in average molecular weight of the polyethylene glycol (PEG) component. Because the desired permeation enhancing effect is more pronounced with the lower molecular weights of about 200–400, $PEG_{200-400}$ ML is preferred according to this invention. PEGML has a permeation enhancing effect on the transport of drugs through body surface tissues generally in addition to the skin. Nevertheless, because skin is one of the most effective of the body's barriers to permeation of foreign substances, the effect of PEGML on skin permeation makes it extremely useful in transdermal drug delivery. The following description of preferred embodiments of the invention is therefore directed primarily to improving transdermal delivery of drugs.

Referring now to FIG. 1, a transdermal therapeutic system 1 according to this invention is shown which comprises a drug/permeation enhancer reservoir 2 in the form of a matrix containing the and PEGML. The reservoir 2 is covered by an impermeable backing 3 which is preferably sized slightly larger in circumference than reservoir 2. Means 4 for maintaining the system on the skin may either be fabricated together with or provided separately from the remaining elements of the system which means in the embodiment of FIG. 1 takes the form of an adhesive overlay. The use of an adhesive overlay with this invention is preferred to the use of an in-line adhesive applied to the skin proximal surface of reservoir 2 because PEGML adversely affects the adhesive properties of most pharmaceutically acceptable contact adhesives. For this reason, impermeable backing layer 3 is preferably sized slightly larger than the reservoir 2 to provide a peripheral area around reservoir 2 free of PEGML to prevent adverse interaction between the adhesive in the overlay 4 and any of the PEGML which may seep from under the base of reservoir 2 in use. A strippable release liner 5, adapted to be removed prior to application would normally be included in the packaged product.

Various materials suited for the fabrication of the various layers are disclosed in the aforementioned patents. The composition of the matrix may, depending, on the drug to be delivered, be either aqueous based or anhydrous and suitable matrices or carriers described in the above identified patents.

Preferably the matrix should have sufficient solubility for PEGML to act as a reservoir for the desired time of administration and include, without limitation, natural and synthetic rubbers such as polybutylene, polyisobutylene, polybutadiene, polyethylene, styrenebutadiene copolymers, polyisoprene, polyurethane, ethylene/propylene copolymers, polyalkylacrylate polymers, copolyesters, ethylene/acrylic copolymers, silicones and butadiene/acrylonitrile copolymers for example and other polymers such as the ethylene vinylacetate (EVA) polymers described in U.S. Pat. No. 4,144,317 (which is incorporated herein by reference), for example, gelled or thickened mineral oil, petroleum jelly and various aqueous gels and hydrophilic polymers. Typically the drug is dispersed through the matrix or carrier at a concentration in excess of saturation, the amount of the excess being a function of the intended useful life of the system. The drug, however, may be present at initial levels below saturation without departing from this invention. The PEGML is preferably dispersed through the matrix at a concentration sufficient to provide permeation enhancing concentrations of PEGML in the reservoir throughout the anticipated administration time.

In addition to the drug and PEGML, which are essential to the invention, the matrix may also contain other materials such as dyes, pigments, inert fillers or other permeation enhancers, excipients, and conventional components of pharmaceutical products or transdermal therapeutic systems as known to the art.

Figure 2:
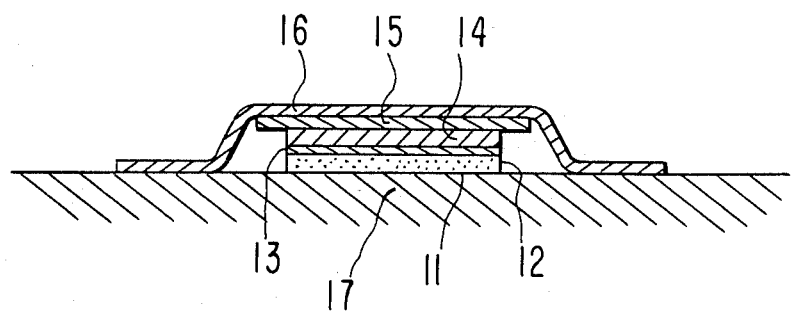
FIG. 2 is a cross-sectional view through another embodiment of transdermal therapeutic system according to this invention.

Referring now to FIG. 2 another embodiment of this invention is shown in place upon the skin 17 of a patient. In this embodiment the transdermal therapeutic system 10 comprises a multilaminate drug/enhancer reservoir 11 having at least two zones 12 and 14. Zone 12 consists of a drug reservoir substantially as described with respect FIG. 1. Zone 14 comprises a PEGML reservoir which is preferably made from substantially the same matrix as used to form zone 12 and which is substantially free of any undissolved drug. A rate-controlling membrane 13 for controlling the release rate of PEGML from zone 12 to the skin may also be utilized between zones 12 and 14 if desired. Suitable rate-controlling membranes may be formed from polymers having a permeability to PEGML lower than that of zone 12.

An advantage of the system described in FIG. 2 is that the drug loaded zone 12 is concentrated at the skin surface rather than throughout the entire mass of the reservoir. This functions to reduce the amount of drug in the system while maintaining an adequate PEGML supply.

Superimposed over the drug/enhancer reservoir 11 is an impermeable backing 15 and adhesive overlay 16 as described above with respect to FIG. 1. In addition, a strippable release liner (not shown) would preferably be provided on the system prior to use as described with respect to FIG. 1 and removed prior to application to the skin 17.

In the embodiments of FIGS. 1 and 2 the carrier or matrix material has sufficient viscosity to maintain its shape without oozing or flowing. If the matrix or carrier is a low viscosity flowable material, the composition can be fully enclosed in a pouch or pocket between the impermeable backing and a permeable or microporous skin contacting membrane as known to the art from U.S. Pat. No. 4,379,454, noted above, for example. Although the invention is most useful with drugs whose permeability is too low for therapeutic effects to be obtained in the absence of an enhancer; its use with systems employing drug rate controlling membranes such as disclosed in U.S. Pat. Nos. 3,598,122 and 3,598,123 noted above is also contemplated. In the absence of PEGML the flux of estradiol through skin is too low to form a comparable sized system.

EXAMPLE I

A transdermal therapeutic system for administration of 17-β estradiol was formulated from 2.5% estradiol, 20% PEG$_{200}$ML and 77.5% natural rubber by mixing the estradiol with the rubber latex and casting and drying the resultant mixture to a thickness of about 9 mils. The PEG$_{200}$ML was imbibed into the drug loaded matrix from a saturated solution of estradiol in PEGML and discs 10.5 cm$^2$ were cut from the resultant product. The systems so produced were applied to a human subject by means of an adhesive overlay for 7 days and estradiol blood levels measured. The estradiol level rose rapidly to about 40 pico g/ml within about 10 hours and remained in the range of about 35 to 55 pg/ml until the systems were removed. No pain or discomfort was noted during wearing nor was there any unacceptable erythema 24 hours after removal.

EXAMPLE II

Transdermal therapeutic systems for administering 17-β estradiol were formulated from 2.5% estradiol, 5% Cabosil® silicon dioxide, 6% PEG$_{200}$ML and 86.5% Polyisobutene (PIB)-mineral oil (MO) adhesive consisting of 22% high molecular weight PIB, 28% low molecular PIB weight and 50% MO by solvent casting from heptane solution into a 9 mil thick film. After evaporation of all solvent 7.5 cm$^2$ plugs were cut and applied to a human subject by means of an adhesive overlay for seven days. No pain, irritation or erythema was reported.

EXAMPLE III

A bilaminate transdermal therapeutic system as described with respect to FIG. 2 for the delivery of progesterone was fabricated from 20% PEG$_{200}$ML, 40% EVA$_{40}$ and 40% tackifier (Staybelite Ester #10, Hercules Inc.) as the enhancer reservoir and 5% progesterone, 20% PEG$_{200}$ML, 37.5% EVA 40 and 37.5% tackifier (Staybelite Ester #10) as the reservoir layer. The layers were sequential solvent cast from methylene dichloride and dried one upon the other to produce a drug reservoir layer 3 mil thick and a PEGML reservoir layer 7 mil thick. Plugs 45 cm$^2$ were cut and applied to a human subject for 24 hours. Progesterone blood levels in the range of 20-60 picograms/ml above background peaked at about 5 hours after application and were maintained during the balance of application. No irritation or sensation was noted and no erythema was apparent 24 hours after removal. In the absence of PEGML the flux of progesterone through skin is too low to produce the blood levels noted from comparable sized systems.

EXAMPLE IV

In vitro measurements of cadaver skin permeation of isosorbide dinitrate (ISDN) and nitroglycerin (NG) from drug loaded PIB/MO matrices containing 5% PEG$_{200}$ML and the drug on lactose carrier at loadings of 1.25 and 1.6 mg/cm$^2$ into an infinite aqueous sink at 32° C. were measured and compared to the in vitro drug flux from existing PEGML free ISDN (ISOKET) and NG (Nitro-Bid ®) systems having higher drug loadings of 2.5 mg/cm$^2$. The flux from the ISDN sample according to this invention was in the range of about 20-21 μg/cm$^2$/hr from approximately 2-25 hours. The flux from the ISOKET system was in the range of about 12-13 μg/cm$^2$/hr for the same time period. The NG flux from the sample according to this invention was in the range of about 15-19 μg/cm$^2$/hr from approximately 1-27 hours whereas the flux from the Nitro-Bid ® system was in the range of about 5-13 μg/cm$^2$/hr during the same time period.

Having thus generally described our invention and having provided specific embodiments thereof it will be readily apparent to workers skilled in the art that various modifications and substitutions can be made without departing from the scope of this invention which is limited only to the following claims, wherein:

We claim:

1. A composition of matter for application to a body surface or membrane to deliver a biologically active agent by permeation through a body surface or membrane comprising, in combination; a biologically active agent and a permeation enhancing amount of polyethylene glycol monolaurate.

2. The composition of claim 1 when said agent and polyethylene glycol monolaurate are dispersed within a carrier therefor.

3. The composition of claim 2 wherein said agent is present in an amount in excess of its saturation concentration in the carrier.

4. The composition of claim 1 wherein the polyethylene glycol component of said polyethylene glycol monolaurate has an average molecular weight in the range of about 200-400.

5. The composition of claims 1, 3, or 4 wherein said body surface or membrane is intact skin.

6. A transdermal therapeutic system comprising the composition of claims 1, 2, 3 or 4 in combination with:
   (a) an occlusive backing behind the skin distal surface of said composition, and
   (b) means for maintaining said composition in agent and polyethylene glycol monolaurate transferring relationship to intact skin.

7. A method for enhancing the flux of a biologically active agent through a body surface or membrane which comprises placing a source of said agent in agent transmitting relationship to said surface or membrane in the presence of a permeation enhancing amount of polyethylene glycol monolaurate.

8. The method of claim 7 wherein the source of said agent contains agent in excess of its saturation concentration in said source.

9. The method of claim 7 or 8 wherein said body surface or membrane is intact skin.

10. In a method for administering a biologically active agent by permeation through an intact body surface which comprises:
  (a) placing a source of said agent and a permeation enhancer therefor in agent and permeation enhancer transmitting relationship to said body surface, and
  (b) maintaining said source in contact with said body surface for a period of time sufficient to produce a beneficial effect; the improvement wherein said permeation enhancer is polyethylene glycol monolaurate.

11. The method of claim 10 wherein said body surface is the skin.

12. The method of claim 11 wherein the polyethylene glycol component of said polyethylene glycol has an average molecular weight of about 200–400.

13. In a transdermal therapeutic system comprising:
  (a) a source of a transdermally deliverable biologically active agent,
  (b) a source of a skin permeation enhancer for said agent and
  (c) means for maintaining said system in agent and permeation enhancer transferring relationship to intact skin; the improvement wherein said permeation enhancer is polyethylene glycol monolaurate.

14. The system of claim 13 wherein said agent is present in said source at a concentration above saturation.

15. The system of claim 12 wherein said PEGML is $PEG_{200-400}ML$.

16. The system of claim 13 wherein said agent is present at a concentration sufficient to maintain the concentration above saturation for an extended period of time and said PEGML is present at a concentration sufficient to provide permeation enhancement throughout said extended period of time.

* * * * *